United States Patent
Suzuki et al.

(10) Patent No.: US 7,276,046 B1
(45) Date of Patent: Oct. 2, 2007

(54) LIQUID CONDUCTIVE COOLING/HEATING DEVICE AND METHOD OF USE

(75) Inventors: Fred K. Suzuki, Arlington Heights, IL (US); Lawrence C. Mead, Hoffman Estates, IL (US); Dick One', deceased, late of Palatine, IL (US); by May S. One, legal representative, Palatine, IL (US)

(73) Assignee: Biosynergy, Inc., Chicago, IL (US)

( * ) Notice: Subject to any disclaimer, the term of this patent is extended or adjusted under 35 U.S.C. 154(b) by 566 days.

(21) Appl. No.: 10/298,800

(22) Filed: Nov. 18, 2002

(51) Int. Cl.
*A61F 7/12* (2006.01)
(52) U.S. Cl. ............... 604/113; 604/114
(58) Field of Classification Search ......... 604/113, 604/114, 4.01, 6.13; 606/24, 27; 607/96, 607/98, 99; 165/156, 163, 184
See application file for complete search history.

(56) References Cited

U.S. PATENT DOCUMENTS

| | | | | |
|---|---|---|---|---|
| 675,647 A * | 6/1901 | Andersen et al. | ......... | 604/113 |
| 911,405 A * | 2/1909 | Hendrix | ......... | 165/156 |
| 1,569,499 A * | 1/1926 | Kagi | ......... | 165/156 |
| 1,819,941 A * | 8/1931 | Brown | ......... | 604/114 |
| 2,087,586 A * | 7/1937 | Tishman | ......... | 392/496 |
| 3,326,283 A * | 6/1967 | Ware | ......... | 165/181 |
| 3,612,059 A | 10/1971 | Ersek | | |
| 3,696,861 A * | 10/1972 | Webb | ......... | 165/133 |
| 3,768,149 A * | 10/1973 | Swaney, Jr. | ......... | 29/527.2 |
| 3,768,290 A * | 10/1973 | Zatell | ......... | 72/68 |
| 4,179,911 A * | 12/1979 | Saier et al. | ......... | 72/78 |
| 4,353,234 A * | 10/1982 | Brothers et al. | ......... | 72/98 |
| 4,359,086 A * | 11/1982 | Sanborn et al. | ......... | 165/133 |
| 4,532,414 A * | 7/1985 | Shah et al. | ......... | 392/470 |
| 4,796,696 A | 1/1989 | Stocton et al. | | |
| 4,878,537 A | 11/1989 | Verkaart | | |
| 5,370,674 A | 12/1994 | Farrell | | |
| 5,474,538 A | 12/1995 | Stihler et al. | | |
| 6,427,767 B1 * | 8/2002 | Mougin | ......... | 165/133 |
| 6,428,747 B1 * | 8/2002 | Dueri et al. | ......... | 422/46 |

* cited by examiner

*Primary Examiner*—Sharon E. Kennedy
(74) *Attorney, Agent, or Firm*—Vedder, Price, Kaufmann & Kammholz, P.C.; W. Dennis Drehkoff

(57) ABSTRACT

A device for heating or cooling medical fluids to be administered to a patient is disclosed. The device comprises a hollow, cylindrical heat/cold exchanging body having external grooves for receiving flexible tubing, the body comprising conductive material for transferring heat or cold from the medical fluid flowing to the patient. A method of using the device is also disclosed.

18 Claims, 3 Drawing Sheets

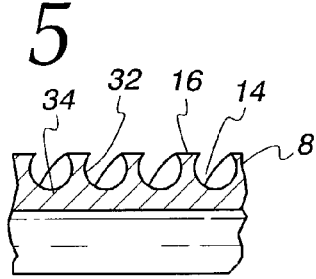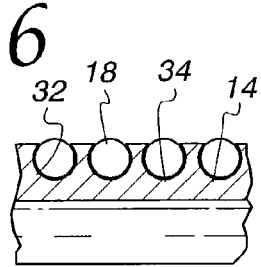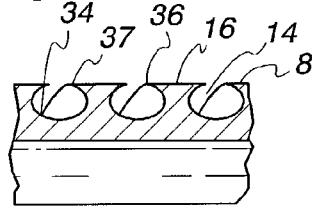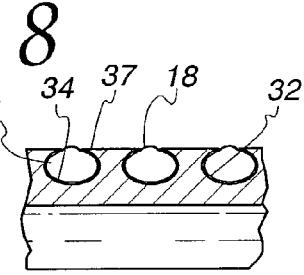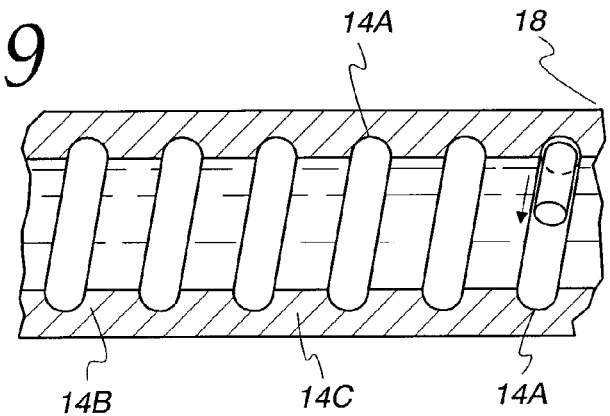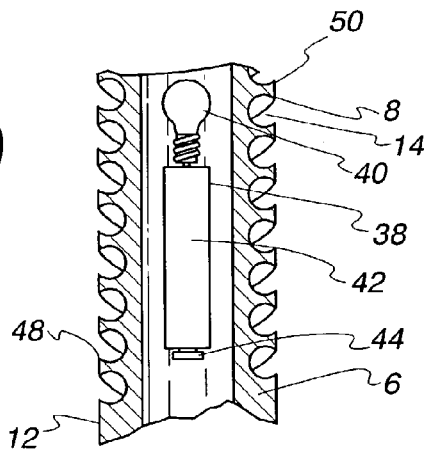

LIQUID CONDUCTIVE COOLING/HEATING DEVICE AND METHOD OF USE

BACKGROUND OF THE INVENTION

This invention relates to a device for moderating the temperature of physiological or medical fluids. More particularly, this invention relates to the transfer bio-conduction of cold or hot energy from blood or other fluids before the blood or fluids are infused into a patient.

It is established that rapid infusion of cold blood and other cold fluids may cause a recipient's heart to stop. Complications caused by rapid infusion of cold blood or other fluids may be prevented by allowing the blood or fluid to warm as it passes through the delivery tubing on its way to the patient.

Rapid infusion of large amounts of fluid, plasma or blood, that are stored at low temperatures, approximately 4° C., can result in hypothermia. Patients at the greatest risk of infusible materials are the elderly, severely traumatized or with prolonged hypotension. Those who are undergoing open-heart surgery or abdominal surgery also suffer heat loss. The adverse effects of hypothermia include depressed myocardial function, increased hemoglobin oxygen affinity, and decreased hepatic metabolism of citrate. Direct infusion of 4° C. blood into the central circulation is dangerous. In cardiac surgery, a cardioplegic solution is used in an attempt to stop the heart, adding to the threat of imminent injury or death. It is known that hypothermia can adversely affect platelet function, the coagulation cascade and thus contributes to the bleeding associated with massive transfusion.

It is also known that during surgery blood and other fluids are heated to approximately body temperature of the patient. There are situations when inadvertently these fluids are warmed to a temperature in excess of the desired temperature (98-100° F.). The fluid at a high temperature may cause complications to the patient.

The prior art has tried to solve problems associated with the infusion of cold blood, which would result in hypothermia, and the infusion of warm blood, that is, over the temperature of 30° C., or other liquids by designing devices which have means for wrapping a tubing which carries blood or other fluid around a conducting unit, so that the unit may conduct cold or heat from the fluid passing through the tubes. Methods of warning often involve the use of electrical heat exchange coils. Other devices rely on the availability of AC/DC electrical current and need to be monitored.

U.S. Pat. No. 5,473,538 to Stihler et al. discloses an apparatus for heating fluids having a cylindrical heat exchanging body with outer grooves for holding a tubing or conduit through which the fluid flows. The groove for holding the tubing forms windings around the cylindrical body which emphasizes the number of windings per length of tubing for heat transfer. For example, with a fixed section length l to be warmed in the tubing, the heat transfer length L per winding W is at least increased by a factor of 1.4 or the heat-exchanging cylinder is directed largely horizontally and the diameter of the heat exchanging body is larger than or equal to 160 millimeters. This disclosure is limited to having a relatively large heat exchanging body so that the surface area of the tubing is in contact with it for a relatively long length of the tubing. This is required for heat transfer. More specifically, the length l per winding W assumes the value of at least 52 cm and the groove is fashioned in the vicinity of the opening from a heat insulating material or is coated with a heat insulating material.

The heat exchanging length l is defined as follows:

$$l = \pi \times d \pi w$$

whereby d corresponds to the diameter of a straight circular cylinder minus twice the groove depth.

U.S. Pat. No. 5,370,674 issued to Farrell discloses a method of heating blood and fluid to a temperature appropriate for administration to a patient. The fluid is maintained at a desirable temperature during the procedure. The fluid in the tubing passes through an elasticized device incorporating a semi-solid composition with a relatively high heat capacity, which is preheated to the desired temperature for the fluid so that temperature transfer can take place prior to administration of the fluid to the patient.

U.S. Pat. No. 4,796,696, issued to Stockton et al., describes a heat exchange in the form of a hollow container. Catheters are placed inside the container adjacent to and touching the walls of a heat exchanger so that heat transfer may take place. The volume of the open area of the container is large, thereby allowing a significant amount of the tubing to be placed inside the container and heated.

U.S. Pat. No. 4,878,537, issued to Verkaart, discloses a heat exchanger used for heating physiological fluids which includes an inner tube, an outer tube, and a space between the two tubes for receiving a fluid. A warming fluid passes through the inner tube, which transfers through the tube to heat the fluid passing between the inner tube and the outer tube.

U.S. Pat. No. 3,612,059, issued to Ersek, describes a heat exchange fabricated to form a pair of thin flexible films bonded to form a pair of flow channels which are disposed in a parallel manner. On a top surface of the flexible film, there is a metallized reflective coating, and on the bottom is a black coating. Blood flows through the open channels formed by the pair of flexible films. The device is intended to be worn on the body of the patient and utilizes the patient's body heat for controlling the temperature of intravenous fluids being infused into the patient.

The disadvantage of conventional devices is that they may require the use of electricity to warm fluids for intravenous administration which are cumbersome and must be positioned close to the patient. Further, conventional tube-like pre-heated devices rapidly cool and after a short time are no longer effective. Other devices which may require the wrapping of flexible tubing in outer grooves are large and cumbersome. There is a need for a non-electrical, small diameter, liquid conductive cooling/heating device that is disposable and fits within one's hand for facile and convenient use.

SUMMARY OF THE INVENTION

This invention is a small, disposable and simple device for providing continuous heating or cooling of medical fluids which are administered to patients, particularly for patients undergoing intravenous fluid administration during surgery and/or post-operative recovery. The device does not use electricity for heating or cooling the medical fluids. The heating or cooling is accomplished by conduction which is a process for transporting energy (hot/cold) in a medium from one location to another without the involvement of any visible movement. The mechanism or energy transfer is classified as energy transfer by convection:

$$\frac{\Delta Q}{\Delta t} = \frac{kA\Delta T}{d}$$

The device of the present invention comprises a hollow cylindrical heat exchanging body having an outer groove for accepting flexible tubing. The device and groove comprise conductive material for transferring heat or cold from the fluid flowing through the flexible tubing.

In one embodiment of the invention the groove has sidewalls which contact about 66% of the circumference of the round flexible tubing that is inserted between the sidewalls. This is advantageous for a large amount of the surface area of the flexible tubing contacts the device thereby allowing for more rapid dissipation of heat and cold from the fluid passing in the flexible tubing. The flexible tubing typically has an outside diameter of about 3/16 inch and it may be readily fitted within the outer grooves of the device. The fluids passing through the flexible tubing in the grooves may lose or gain temperature due to the contact of the flexible tubing with the conductive material comprising the device.

When winding the flexible tubing into the outer groove of the heat exchanging body, the flexible tubing is pressed or manipulated into the groove by hand. The tubing runs from a valve on the tubing continuing to a receptacle for holding the medical fluids on one end. The opposite end is connected to an appropriate device for insertion into a patient. The deeply configured groove holds the flexible tubing in place. Thus, the winding of the tubing onto the heat exchanging body may commence at either end of the device for convenience of the medical personnel using it.

In another embodiment, the device for heating a medical fluid comprises a heating device for warming medical fluids. The warming device is placed inside the hollow cylindrical heat exchanging body to provide a source of heat to increase the rate of warming the medical fluid passing through the flexible tubing.

In another embodiment, the device for heating a medical fluid comprises a coating of a heat absorption material. The coating may assist in the transfer heat absorbed from the atmosphere to the heat exchanging body to promote the warming of the medical fluid within the flexible tubing in the groove of the heat exchanging body.

Further advantages can be derived from the description and the accompanying drawings. The above mentioned features and those which are further described below can be likewise utilized in accordance with the invention individually or collectively in arbitrary combination. The embodiments mentioned are not to be considered an exhaustive enumeration, but are for exemplary purposes only.

BRIEF DESCRIPTION OF THE DRAWINGS

FIG. 5 shows a cross section of FIG. 2 wherein only the groove is shown without the flexible tubing.

FIG. 6 shows a cross-section of FIG. 2 with round flexible tubing in the grooves of the heat exchanging body;

FIG. 7 shows a cross-section of another embodiment wherein grooves are present which are configured with a lip to contact about 66% of the circumference of the round flexible tubing;

FIG. 8 shows a cross-section of FIG. 7 with round flexible tubing in the grooves of the alternative embodiment;

FIG. 9 shows a cross-section of another embodiment of the present invention wherein a groove is present within the circular walls of the heat exchanging body of the present invention; and, FIG. 10 shows a cross-section of the heat exchanging body of the present invention containing means for heating medical fluid as it passes through the flexible tubing.

DETAILED DESCRIPTION OF THE INVENTION

Figure 1:
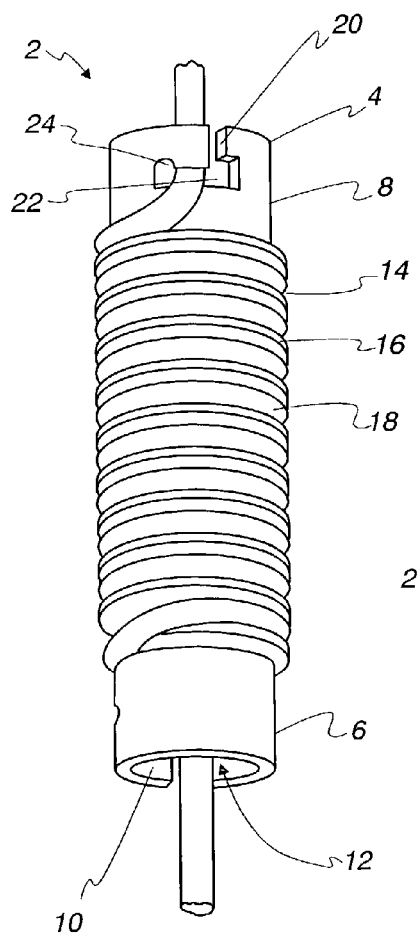
FIG. 1 shows a device for warming or cooling medical fluids in a perspective view with a heat exchanging body and flexible tubing present therein.

With reference to FIG. 1, a heat/cold exchanging device 2 in accordance with the invention is shown having a first end 4 and an opposite or second end 6. The distance between the first end 4 and second end 6 is preferably about 1.78 cm so that the compact device can fit on the palm of a hand. The small size renders the device convenient for use. The heat/cold exchange device is cylindrically shaped with an outside wall 8 and inside wall 10 defining a hollow space 12. Preferably, the diameter inside of the cylindrically shaped inside wall 10 is about 0.49 cm. Grooves 14 are formed on the surface of outside wall 8. The grooves 14 are defined or separated from each other by walls 16. The grooves may be of any suitable width for holding a flexible tubing 18, the width being dependent on the width of the tubing. Typically, plastic flexible tubing used in the present invention will have an outside diameter of about 3/16 inch with an inside diameter of about 1/8 inch. The grooves 14 run spirally around the outside wall 8 of the device.

The tubing 18 is shown engaging grooves 14 exposing walls 16 between the wrapped flexible tubing. At the first end 4 of the device there is a vertical notch 20 with horizontal notch 22 for securely holding flexible tubing 18. The horizontal notch 22 has a rounded catch 24 for placement of the flexible tubing.

Figure 2:
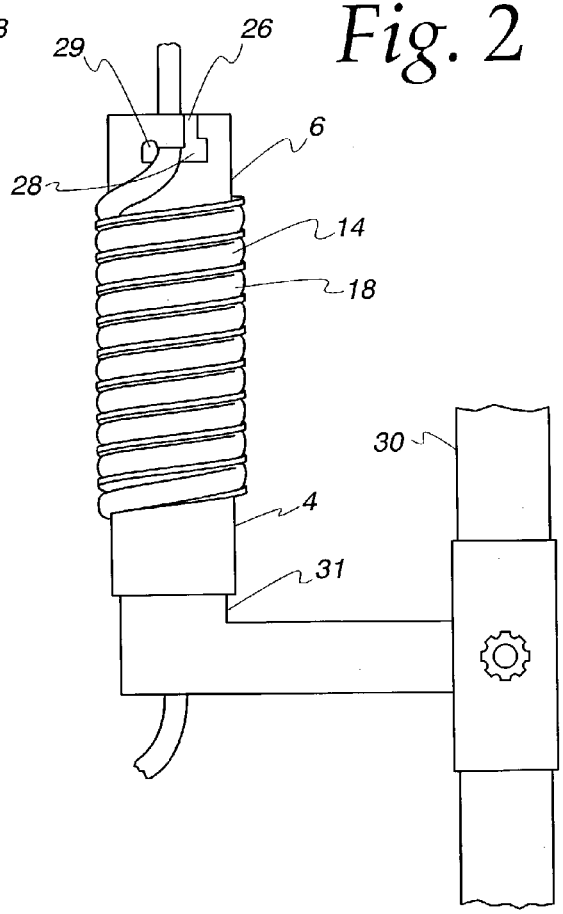
FIG. 2 shows a side view of the device of the present invention connected to a stand showing a groove holding flexible tubing present therein.
Figure 3:
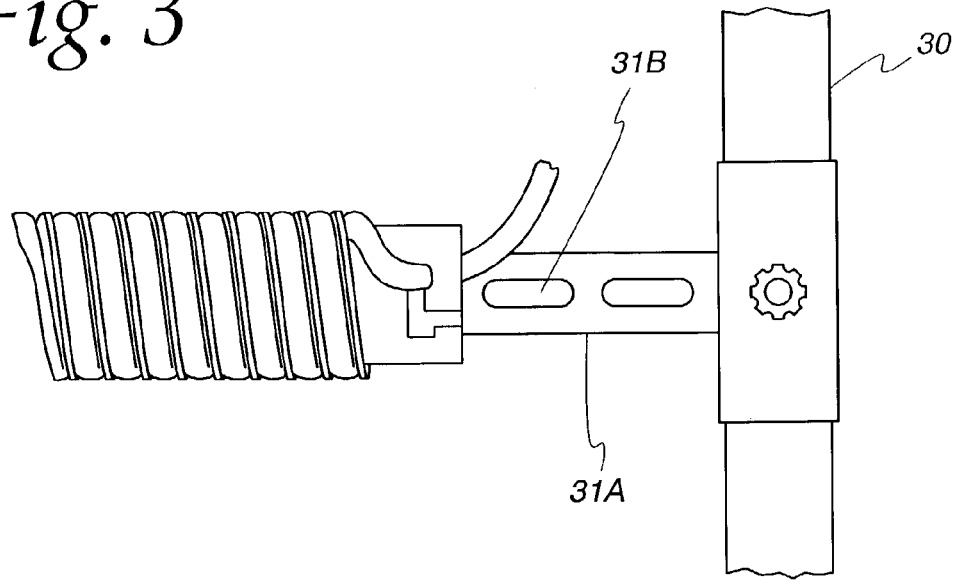
FIG. 3 shows a side view of the device of the present invention connected to a stand in a horizontal position.

FIG. 2 shows a side view of the device of the present invention which also displays at the second end 6 a vertical second notch 26, second horizontal notch 28 and second catch 29. The notches allow the device to be suspended vertically on the tubing between the source of the medical fluids and device for introducing medical fluids into the patient so that the fluid may be heated or cooled by the conductivity of the device of the present invention. Medical fluids may be any physiological fluid or therapeutic fluid administered to a patient in need thereof. Medical fluids may be blood, plasma, saline, a therapeutic agent or the like. The fluid may be cold, at a temperature just above freezing or above 4° C. or hot, at a high temperature above body temperature. The device may be connected to stand 30 in a vertical arrangement, when the flexible tubing may be wrapped onto the device engaging grooves 14 and inserted on a vertically aligned post 31A by hand for facile use. Further, the device may also be placed in a horizontal arrangement attached to stand 30 as shown in FIG. 3 wherein post 31 is positioned perpendicular to stand 30. The horizontal post 31A may contain apertures 31B thereby allowing air flow within the post which may preferably be hollow.

Figure 4:
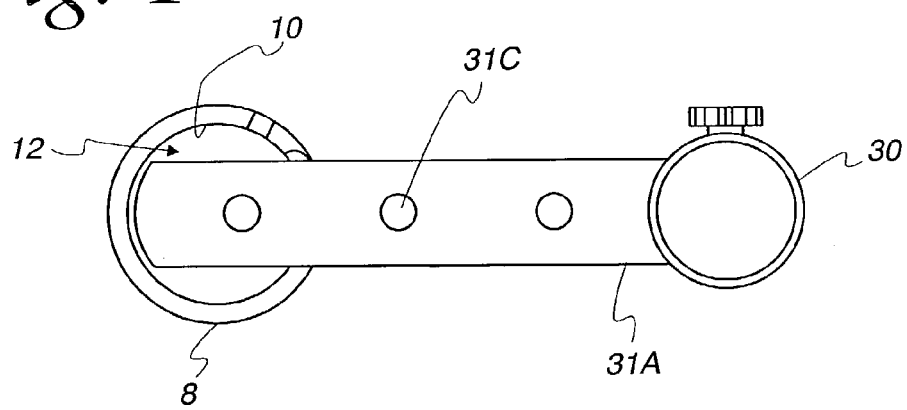
FIG. 4 shows a bottom view of the device of the present invention described in FIG. 2.

FIG. 4 shows a bottom view of FIG. 2 where post 31 contains hollow space 12 and exposes apertures 31C. The bottom view shows inside wall 10 and outside wall 8.

FIG. 5 shows a partial cross-section of the heat/cold exchanging body of the present invention which is made from heat or cold conducting material. The material may be any conductive material that is suitable for the purpose of conducting heat or cold from a fluid passing through a flexible tubing in which the tubing is in contact with the conducting material. The preferred conducting material is aluminum. The figure shows grooves 14 in the outside wall 8 of the device of the present invention. The grooves 14 are separated by walls 16. The grooves have sidewalls 32 that meet at the groove bottom 34 so that the flexible tubing fits securely in the groove. The flexible tubing 18 is easily inserted into groove 14 by press fitting with a finger by medical personnel administering the medical fluids to the patient.

FIG. 6 shows a partial cross section of the device of the present invention with flexible tubing 18 inserted in grooves 14. The groove sidewalls 32 and bottom 34 the medical fluid passing through the flexible tubing 18. Preferably about 50% of the circumference of the flexible tubing 18 is in contact with groove 14 having side walls 32, and groove bottom 34.

FIG. 7 shows an alternate embodiment of the present invention wherein a partial cross section of the device exhibits grooves 14 separated by extended wall 36 to provide for more surface area of the conduction device to be in contact with the round or circular flexible tubing 18, thus allowing for an increased rate of conductivity to heat or cool medical fluids passing through the flexible tubing 18. The extended wall 36 is shaped to be in contact with substantially more of the surface area of flexible tubing than wall 16 of the present invention. Extended wall 36 has lip 37 which, in combination with side walls 32, groove bottom 34 and extended wall 36, contacts up to about 66% of the circumference of the flexible tubing 18 passing through grooves 14. The tubing 18 is loaded into grooves 14 with extended walls 36 by pressure fitting the tubing into the groove by hand of the medical personnel administering medical fluids to a patient.

FIG. 8 shows a partial cross section of an alternate embodiment of the present invention wherein flexible tubing 18 is inserted in groove 14 having side walls 32, groove bottom 34, and extended side wall 36 with lip 37 to intimately contact about 66% of the circumference of the flexible tubing 18 wherein medical fluids flow to a patient.

FIG. 9 shows an alternate embodiment of the present invention wherein groove 14A is bored, preferably spirally, entirely within the width 14B of inside wall 10 and outside wall 8. This embodiment allows contact with the inside 14C of the width 14B with about 100% of the circumference of the flexible tubing 18 passing through. Flexible tubing 18 is inserted in an opening at the first end of the device (not shown) and threaded through the width 14B between the inside wall 10 and outside wall 8 to the second end.

FIG. 10 shows another alternate embodiment of the present invention wherein a heat source 38 is utilized with the present invention. The heat source may be any suitable means for providing heat to the device to assist in the heating of medical fluids passing through flexible tubing 18 in grooves 14 on outer wall 8. A preferred heat source is a light bulb 40 powered by a battery 42 secured by means 44 to connect the battery 42 to the bulb 40. Battery 42 may be attached to connecting means 44, which may comprise conducing material affixed to the battery and bulb, to activate the bulb by inserting it in the second end 6 into hollow space 12 of the cylindrically shaped device. Once the battery is inserted, contact point 48 is inserted into the hollow space so the light bulb 40 can be activiated to provide heat to warm the device and the fluid passing through flexible tubing 18. Further, a heat absorbing material 50 may be applied to the outer wall 8 or inside wall 10 of the device. The heat absorbing material may be any suitable material for absorbing heat from the atmosphere to accelerate the heating of medical fluids passing through tubing 18. The material may preferably be in an appropriate substance having a color, for example black, to absorb heat and therefore allow the device to transfer it to the medical fluid passing through the tubing 18.

The device 2 for heating or cooling medical fluids is a cylindrical body with an inside wall 10, an outside wall 8 which exhibits a groove 14 for the insertion of rounded flexible tubing 18 in which medical fluids pass. Extended walls 36 with lip 37 in a preferred embodiment contacts about 66% of the circumference of the flexible tubing 18 to increase the surface area of the contact point between flexible tubing and device thereby assisting the heating/cooling of the medical fluid. The device is light, easily manipulated for it fits within the palm of one's hand, durable and is disposable. These features facilitate manufacture and use. The device maintains sterility in adequate packaging.

In operation, the device 2 is used in a method of heating or cooling a medical fluid before administration to a patient by fitting a circular flexible tubing 18 having first and second ends, by hand in the outer groove 14 of the hollow cylindrical heat/cold exchanging body of the present invention, said groove and body comprising conductive material, attaching the first end of the flexible tubing to a source of medical fluids and commencing the flow of the medical fluid from the source to the patient, attaching the second end of the flexible tubing to the patient. The medical fluid is heated or cooled by contacting the conductive material of the heat/cold exchanging body.

The warming/cooling of blood or other fluid by the device of the present invention relates to the amount of blood and time of contact of the blood with the heat/cold exchanging body so that the thermal energy of the blood is dissipated by the convection of the energy onto the conducting material of the device.

Blood banks typically store blood at 2-4° C. This temperature must be raised to avoid problems for the infusion recipient. It is conventional wisdom that blood at a temperature of about 10° C. is suitable for infusion. The device and method of the present invention are capable of warming blood from a temperature of 4° C. when leaving the source or bag, up to 10° C. or more as it is infused into a patient in an acceptable time period. After blood is removed from its refrigeration unit, the temperature of its environment will commence warming the blood and continue to do so until it reaches the patient. It has been found that when the ratio of the mass of the fluid to be warmed and the mass of the device 2 of the present invention is about 1:1000 to about 1:1250, the fluid is warmed to an acceptable temperature by the conductive material of the device without electrical energy or any other heat source. This is calculated by observing that one drop of blood weighs, which is similar in density to water, about 0.082 g, with the weight of the device being about 100 g, while traveling at a rate of 40-50 drops per minute in accordance with the conditions described below at room temperature.

Typically, the device 2 of the present invention comprises a heat sink or cold sink material, preferably an aluminum cylinder having dimensions of about 4½inches (1.78 cm) in length and about 1¼inches (0.49 cm) in diameter, which is a compact size for facile, convenient use. The weight of the device 2 is about 100 g. The dimensions of the device are recited for illustrative purposes and are by no means limitative.

The intravenous tubing used with the device of the present invention may be any conventional, round, flexible tubing intended for intravenous administration of medical fluids. Preferably, the flexible tubing is plastic, having a length of about 43$^{13}$/$_{16}$inches (17.9 cm) and a weight of about 11.6 g. About 24 inches of flexible tubing 18 is wrapped into groove 14 in the typically sized device, which may preferably fit within one's hand.

The intravenous needle used with the device of the present invention may preferably be one of 18-21 Gauge, depending on the viscosity of the fluid to be infused and the amount of time required for infusion. Larger diameters of the intravenous needle permit faster or more unencumbered flow the medical fluid through the needle and are more practical for viscosous fluids. For reference, the plastic tubing of the aforementioned dimensions holds about 8.153 mL of distilled water or 8.153 GM. The total weight of the tubing and fluid is about 20.08 GM.

Depending upon various factors, a drop of blood may travel from its source to the patient at different rates. The size of the needle, viscosity of the fluid or blood being administered, the diameter of the flexible tubing, and the walls in grooves 14 of the present invention affect the contact time and flow rate of the blood to the device 2 of the present invention. Typically, blood flowing at a rate of 100 drops/min. through a flexible tubing having an inside diameter of ⅛ inch and a 19 Gauge needle will pass through the tubing, engaging the device of the present invention in about 4 minutes. Slower rates of flow, about 30-50 drops per minute, are more typical in non-emergency situations, and therefore pass through the tubing engaging the device for longer time periods.

With the aforementioned physical dimensions of the tubing and 19 Guage needle, it has been determined that blood will be warmed from about 4° C. as it leaves the bag to about 10° C. as it is infused into the patient at a rate of 40 to 50 drops per minute after a time of about 50 minutes.

Modifications within the scope of the appended claims will be apparent to those skilled in the art.

What is claimed is:

1. A device for heating or cooling medical fluids flowing through flexible circular tubing for administration to a patient comprising a hand-held hollow cylindrical heat/cold exchanging body having an outer groove for accepting the flexible tubing, the groove and body comprising a metal conductive material for transferring heat or cold from the fluid flowing through the flexible tubing, the groove being capable of contacting about 66% of the circumference of the flexible tubing.

2. The device of claim 1 wherein the groove has sidewalls, a bottom and a lip.

3. The device of claim 1 wherein the device is made from a heat and cold conducting material.

4. The device of claim 3 wherein the heat and cold conducting material is aluminum.

5. The device of claim 1 wherein it is disposable.

6. The device of claim 1 wherein a heat-generating device is inserted with hollow cylindrical heat exchanging body.

7. The device of claim 6 wherein the device has a coating of heat absorbing material.

8. The device of claim 1 wherein the device has a coating of heat absorbing material.

9. The device of claim 1 wherein the outer groove has windings defining a spiral path around the outside of the heat exchanging body.

10. The device of claim 1 wherein the device has a first end and a second end, the first end and second having means for attaching the flexible tubing to securely fasten the tubing to the device.

11. A device for heating or cooling medical fluids flowing through a flexible circular tubing for administration to a patient comprising a hand-held hollow cylindrical heat/cold exchanging body having an inside wall and an outside wall and a width in between and a groove for accepting the flexible tubing, the groove being bored between the inside wall and outside wall of the heat/cold exchanging body.

12. The device of claim 11 wherein the groove has sides that contact about 100% of the circumference of the flexible tubing.

13. The device of claim 11 wherein the device is made from a metal heat and cold conducting material.

14. The device of claim 11 wherein the device is made from aluminum.

15. The device of claim 11 wherein it is disposable.

16. The device of claim 11 wherein a heat-generating device is inserted within the cylindrical heat or cold exchanging body.

17. The device of claim 11 wherein the heat-generating device is a light bulb and power source.

18. The device of claim 11 wherein the device has a first end and a second end, the first end and second end having means for attaching the flexible tubing to fasten securely the tubing to the device.

* * * * *